(12) United States Patent
Dmitrieva et al.

(10) Patent No.: US 8,897,517 B2
(45) Date of Patent: Nov. 25, 2014

(54) IMAGING SYSTEM WITH REPORTING FUNCTION AND METHOD OF OPERATION THEREOF

(75) Inventors: Julia Dmitrieva, Bothell, WA (US); Jayne Louise Angela Armfield, Lynnwood, WA (US); Michael R. Vion, Lynnwood, WA (US)

(73) Assignee: Koninklijke Philips N.V., Eindhoven (NL)

(*) Notice: Subject to any disclaimer, the term of this patent is extended or adjusted under 35 U.S.C. 154(b) by 540 days.

(21) Appl. No.: 13/141,630

(22) PCT Filed: Dec. 11, 2009

(86) PCT No.: PCT/IB2009/055712
§ 371 (c)(1),
(2), (4) Date: Jun. 22, 2011

(87) PCT Pub. No.: WO2010/073179
PCT Pub. Date: Jul. 1, 2010

(65) Prior Publication Data
US 2011/0255754 A1    Oct. 20, 2011

Related U.S. Application Data

(60) Provisional application No. 61/140,128, filed on Dec. 23, 2008.

(51) Int. Cl.
G06K 9/00     (2006.01)
G06K 9/32     (2006.01)
G06T 7/60     (2006.01)
G06F 19/00    (2011.01)
A61B 8/00     (2006.01)
A61B 8/08     (2006.01)

(52) U.S. Cl.
CPC . *A61B 8/565* (2013.01); *G06T 7/60* (2013.01); *G06F 19/321* (2013.01); *G06F 19/3487* (2013.01); *G06T 2207/30096* (2013.01); *G06T 2207/10136* (2013.01); *G06T 2207/20101* (2013.01); *A61B 8/08* (2013.01)

USPC .................. 382/128; 382/131; 382/294

(58) Field of Classification Search
USPC ................... 382/128, 131, 294
See application file for complete search history.

(56) References Cited

U.S. PATENT DOCUMENTS 5,538,003 A *  7/1996  Gadonniex et al. ........... 600/445
8,195,417 B2 * 6/2012  Feiweier et al. ................ 702/95

(Continued)

FOREIGN PATENT DOCUMENTS

| JP | 2000276550 A | 10/2000 |
| WO | 2007107918 A1 | 9/2007 |
| WO | 2007140593 A1 | 12/2007 |

OTHER PUBLICATIONS

Ligier, Yves et al "Object-Oriented Design of Medical Imaging Software" Computerized Medical Imaging and Grapics, Pergamon Press, NY vol. 18, No. 2, Mar. 1, 1994, pp. 125-135.

*Primary Examiner* — Matthew Bella
*Assistant Examiner* — Jose M Torres

(57) ABSTRACT

A data acquisition method performed by one or more controllers includes receiving information related to a sequence of a plurality of images. The method further includes receiving, from an ultrasonic probe, image information corresponding to a current image of the plurality of images in the sequence. The method still further includes determining whether a caliper input has been received, and when it is determined that a caliper input has been received: obtaining coordinate information corresponding to one or more locations in the current image, selecting an other image which is different from, and associated with, the current image, and obtaining one or more coordinates corresponding to one or more locations in the other image. The method further includes saving a report including the image information and the coordinate information corresponding to each image of the plurality of images of the sequence.

13 Claims, 6 Drawing Sheets

(56) References Cited

U.S. PATENT DOCUMENTS

2006/0116577 A1* 6/2006 DeWitt .................. 600/437
2006/0253024 A1* 11/2006 Altmann et al. .......... 600/437
2006/0270938 A1 11/2006 Yawata
2009/0060306 A1* 3/2009 Ohuchi et al. ............ 382/131
2010/0215245 A1* 8/2010 Olivan Bescos .......... 382/133

* cited by examiner

IMAGING SYSTEM WITH REPORTING FUNCTION AND METHOD OF OPERATION THEREOF

The present system relates generally to medical imaging systems and, more particularly, to an ultrasound imaging system with an automated acquisition technique, and a method of operation thereof.

Typically, thyroid pathology can be non-invasively performed using ultrasonic thyroid assessment methods. During a commonly performed ultrasound thyroid assessment, a series of two-dimensional (2D) images are acquired and thereafter evaluated by a medical professional such as a radiologist. To obtain these 2D images, a medical technician, such as a sonographer, must manually manipulate a transducer across a patient's neck to obtain desired images of different segments of the patient's anatomy. As proper assessment of thyroid pathology requires evaluation of sagittal and axial planes of the thyroid lobes, the technician must manipulate the transducer in different planes and locations to obtain desired images which correspond with each of the planes. After acquiring images, the sonographer then creates a comprehensive report which includes these images. Accordingly, the sonographer must keep track of the images and manually label then to create a comprehensive and accurate report. However, as the report typically includes many images, each of which requires a proper label and other annotations, this process is difficult to perform and is prone to errors. Further, sonographers who lack experience or are in a rush are more likely to create a report which includes errors.

Moreover, the process of compiling a report is further complicated when thyroid lesions are found, in which case the sonographer must perform an extra procedure of using a caliper in order to determine their size and/or location. The sonographer must then incorporate information about these lesions into the report. This process can be difficult to perform correctly, especially when multiple lesions are found. For example, when using conventional methods, sonographers often lose track of the locations or sizes of lesions, and, therefore, include inaccurate information about these lesions in the report. As used herein, the term "lesion" may refer to an enlarged portion of the thyroid gland that may correspond with a tumor, a mass, a lump, a nodule, a node, a growth, an abnormality, etc. Accordingly, the generated reports are often inaccurate and, therefore, difficult or impossible to analyze.

Accordingly, when analyzing these reports, radiologists must often spend time determining whether the reports are accurate before a further analysis can be made. Further, to properly analyze the reports, radiologists must spend valuable time looking for corresponding sagittal and transverse measurements of a lesion and are often unable to determine the location of a lesion when the annotations are missing or incorrect.

Further, medical professionals may rely upon previous reports to determine whether lesions have grown, as well as a rate of growth for these lesions. Moreover, if a current report is inaccurate, the patient may have to undergo further procedures. Additionally, if a previous report is inaccurate, it cannot be repeated. Accordingly, the data contained in the previous report may not be relied upon to determine, for example, a rate of growth, etc., for a lesion.

Accordingly, there is a need for a system and a method to automate an image-capture process which can be used to capture and record medical image information.

Thus, according to a first aspect of the present system and method, there is disclosed a thyroid lesion "smart exam" auto reporting program which overcomes the disadvantages of the prior art and can easily and conveniently capture and record image information using a "smart exam" protocol which is specific to an organ or vessels (e.g., the thyroid gland, kidney, testes, breast, uterus, ovaries, liver, spleen, heart, arterial or venous system, etc.) It is another aspect of the present system and method to automatically report and label the location and measurement of a lesion and thereafter save this information.

Accordingly, by having an automated image-capturing and -reporting routine, software or computer readable instruction embodied in a computer readable medium, such as any type of memory, the time professionals (such as, for example, radiologists), spend evaluating and diagnosing image information related to a patient can be reduced. Additionally, by saving time, costs can be reduced. Moreover, medical liability can be reduced by ensuring that proper examination procedure is followed.

One object of the present systems, methods, apparatuses and devices is to overcome the disadvantages of conventional systems and devices. According to one illustrative embodiment, a medical imaging system includes an ultrasonic probe; and a controller which may receive information related to a sequence of a plurality of images; receive, from the ultrasonic probe, image information corresponding to a current image of the plurality of images in the sequence; determine whether a caliper input has been received, and when it is determined that a caliper input has been received: obtain coordinate information corresponding to one or more locations in the current image, select a further image which is different from, and associated with, the current image, and obtain coordinate information corresponding to one or more locations in the further image. The controller may also save a report including the image information and the coordinate information corresponding to each image of the plurality of images of the sequence. According to the present system, the further image may correspond with an image plane which is orthogonal to an image plane of the current image.

Moreover, according to another aspect of the present system, the controller may receive, from the ultrasonic probe, the image information corresponding to each of the plurality of images in: the sequence when the controller determines that a caliper input has not been received; and a further sequence different from the sequence, when the controller determines that a caliper input has been received. The controller may modify the sequence when the controller determines that a caliper input has been received. Further, the controller may associate a unique view label with each of the images of the plurality of images.

The controller may also receive, from the ultrasonic probe, the further image and/or output a request that coordinate information corresponding to one or more locations in the further image be input.

According to yet another aspect of the present system, there is disclosed a data acquisition method performed by a controller, the method may include the acts of: receiving information related to a sequence of a plurality of images; receiving, from an ultrasonic probe, image information corresponding to a current image of the plurality of images in the sequence; determining whether a caliper input has been received, and when it is determined that a caliper input has been received: obtaining coordinate information corresponding to one or more locations in the current image, selecting, by the controller, a further image which is different from, and associated with, the current image, and obtaining one or more coordinates corresponding to one or more locations in the further image. The method may also include the act of saving a report comprising the image information and the coordinate information corresponding to each image of the plurality of images of the sequence. According to another aspect of the present method the further image may correspond with an image plane which is substantially orthogonal to an image plane of the current image.

According to yet a further aspect of the present method, the controller may receive, from the ultrasonic probe, image information corresponding to each of the plurality of images in: the sequence when it is determined that a caliper input has not been received; and/or a further sequence different from the first sequence, and when it is determined that a caliper input has been received.

According to another aspect of the present method, the image information may include information related to the plurality of images which are to be acquired in a predetermined order. The predetermined order may include a first sequence when a caliper request is not received; and a second sequence different from the first sequence when a caliper request is received. The method may further include the act of modifying the sequence and when it is determined that a caliper input has been received. The method may further include the acts of associating a unique view label with each of the images of the plurality of images, and/or displaying a caliper or outputting a request that one or more coordinates corresponding to one or more locations in the further image be input, when the further image is received.

According to yet another aspect of the present system, there is disclosed a computer program stored on a computer readable memory medium, the computer program may be configured to receive image information from an ultrasonic probe. The computer program may include: a program portion configured to receive information related to a sequence of a plurality of images; a program portion configured to receive, from an ultrasonic probe, image information corresponding to a current image of the plurality of images in an image sequence; and/or a program portion configured to determine whether a caliper input has been received, and when it is determined that a caliper input has been received: to obtain coordinate information corresponding to one or more locations in the current image, to select, by the controller, a further image which is different from, and associated with, the current image, and to obtain coordinate information corresponding to one or more locations in the further image. The computer program may also include a program portion configured to save a report comprising the image information and the coordinate information corresponding to each image of the plurality of images of the sequence.

According to yet another aspect of the present system, the computer program, the further image may correspond with an image plane which is substantially orthogonal to an image plane of the current image. Further, the computer program may also include a program portion configured to receive, from the ultrasonic probe, image information corresponding to each of the images in: the sequence when it is determined that a caliper input has not been received; and a further sequence different from the first sequence, when it is determined that a caliper input has been received.

According to another aspect of the present system, the computer program may include a program portion configured to modify the sequence when it is determined that the caliper input has been received. Further, the computer program may include a program portion configured to associate a unique view label with each of the images of the plurality of images. The computer program may also include a program portion configured to output a request that one or more coordinates corresponding to one or more locations in the further image be input. This request may be output to a user via a speaker, a display, or other suitable method.

Further areas of applicability of the present apparatuses, devices, systems and methods will become apparent from the detailed description provided hereinafter. It should be understood that the detailed description and specific examples, while indicating exemplary embodiments of the systems and methods, are intended for purposes of illustration only and are not intended to limit the scope of the invention.

These and other features, aspects, and advantages of the apparatus, systems and methods of the present invention will become better understood from the following description, appended claims, and accompanying drawing where:

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

In one embodiment, there is provided system, application, and/or method for systematically performing a medical assessment of an organ, such as, for example, a thyroid, so as to standardize medical image reporting, which can reduce evaluation times and errors. Accordingly, medical costs due to acquiring, reporting, and/or evaluating medical images can be reduced.

Figure 1A:
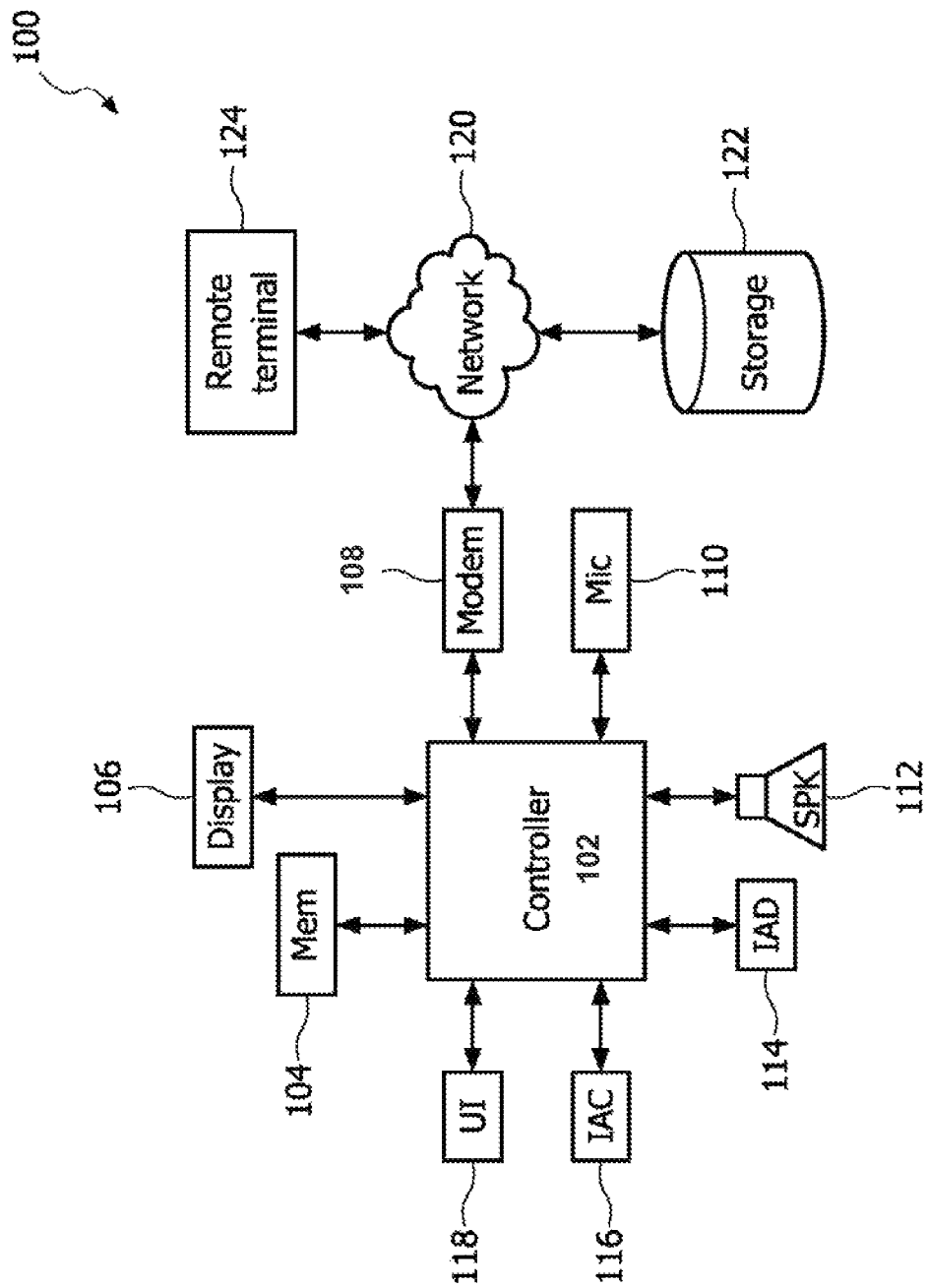
FIG. 1A is a schematic view of an embodiment of the image-capturing system according to the present system.

A schematic view of an embodiment of an image-capturing system 100 according to one embodiment of the present system is illustrated in FIG. 1A. The image-capturing system 100 may include one or more of a controller 102, a memory 104, a display 106, a modem 108, an audio input device (MIC) 110, an audio output device (SPK) 112, an image acquisition device (IAD) 114, an image acquisition control (IAC) device 116, a user interface (UI) 118, a network 120, a remote storage device 122, and a remote device or terminal 124.

The controller 102 controls or is configured to control the overall operation of the image-capturing system 100 and may include one or more controllers which may be located at one or more locations. For example, one or more of the controllers may be located at the remote device 124. Accordingly, certain actions performed by one or more of the processes or the present invention may be performed at the remote device 124.

The memory 104 may interface with the controller 102 and may store or be configured to store programs and data which may be read and/or stored by the image-capturing system 100. The memory 104 may include one or more of a hard disc, a read-only memory (ROM), a random-access memory (RAM), a flash drive, an optical drive, and/or other suitable memory device. Further, the memory 104 may include different types of memory and may be located at a plurality of locations. The memory may include the programs and/or data created by operation of the present systems, devices, and/or methods.

The display 106 may display information under the control of one or more controllers such as, for example, the controller 102. The display 106 may include any suitable display such as, for example, cathode ray tubes (CRTs), liquid crystal displays (LCDs), plasma displays, touch screens, etc. The display 106 may include multiple displays which may be located at different locations. The display 106 may also receive user inputs.

The modem 108 may operate under the control of the controller 102 and may transmit and/or receive data to/from the controller 102 to various locations via, for example, the network 120. The modem 108 may include any suitable modem or modems and may communicate via a wired and/or a wireless link.

The audio input device 110 (MIC) may include any suitable device for inputting audio information, such as, for example, a microphone or transducer. The audio input device 110 may transmit received audio information to the controller 102 via, for example, a coder/decoder (CODEC). The audio input device 110 may also be located at a remote location and may transmit information via, for example, the network 120. The audio input device 110 may receive audio inputs from, for example, a user. A voice recognition program may then translate these commands for use by the controller 102.

An audio output device 112 (SPK) may output audio information for a user's convenience. The audio output device 112 may include a speaker and may output audio information received from, for example, the controller 102, via the CODEC. Further, a translation program may translate a parameter to be visually output on the display 106, so that the parameter can also be output via the speaker 112.

The image acquisition probe or device (IAD) 114 may obtain desired information under the control of the controller 102 and transmit this information to the controller 102 where it may be processed. The IAD 114 may include one or more transducer arrays, etc. For example, the present system may include a transducer such as, for example, a C5-1 transducer by Philips Electronics.

The image acquisition control (IAC) device 116 may be controlled by the controller 102 and may include stabilization control devices (e.g., array stabilizers, etc.) which may control the position of the image acquisition probe (IAD) 114. For example, the IAC device 116 may include one or more devices to control the yaw, pitch, and/or roll of, for example, one or more transducer arrays relative to a handle, etc. Accordingly, the IAC device 116 may control the position of the one or more transducer arrays about an x, y, or z axis and/or reduce undesired harmonics, vibration, etc. Further, the IAC device 116 may include a counter balance, a motor, a control system, etc. to control vibration, etc. of the one or more transducer arrays.

The user interface (UI) or user input device 118 may receive user inputs and transmit these inputs to, for example, the controller 102. The user input device 118 may include any suitable input device which can receive a user input, such as, a keyboard, a mouse, a touch pad, a track ball, a pointer, a digitizer, a touch screen, a finger-print reader, etc. Further, the user input device may include a biometric reader for inputting biometric information such as, for example, the fingerprint reader, an iris reader, etc.

The network 120 may include a local area network (LAN), a wide area network (WAN), the Internet, an intranet, a proprietary network, a system bus, and/or other transmission devices (active and/or passive) which may transmit information between various devices of the image-capturing system 100. The network 120 may operate using any suitable transmission scheme.

The remote storage device 122 may include any suitable memory device which can store information as required by the image-capturing system 100. Accordingly, the remote storage device 122 may include memory devices such as those described with reference to the memory 104. Further, the remote storage device may include a redundant array of independent disks (RAID) and/or other storage configurations. Moreover, the remote storage device 122 may include, for example, a storage area network (SAN). The remote storage device 122 may transmit/receive information to/from the controller 102 via the network 120 and/or the modem 108.

Figure 1B:
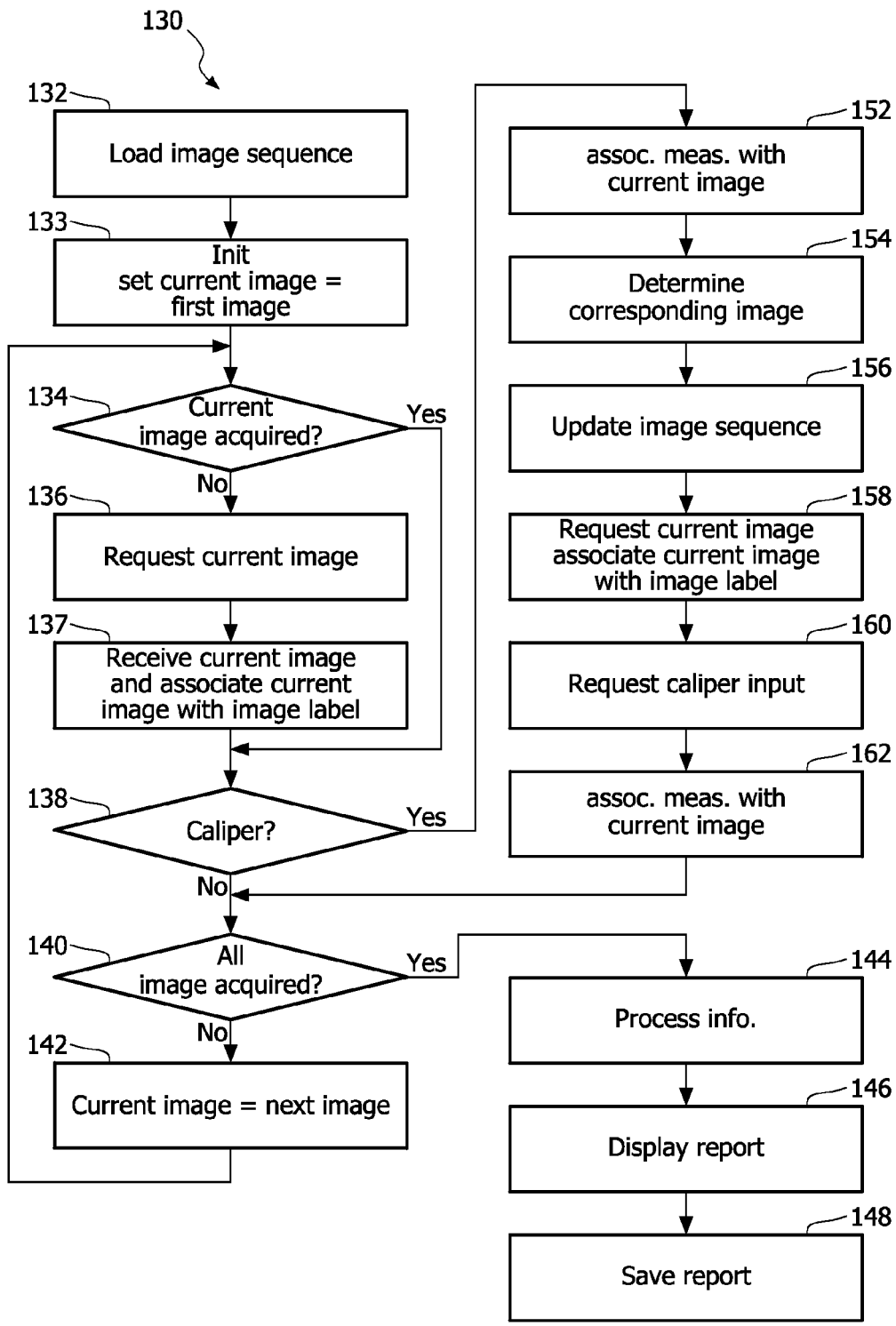
FIG. 1B is a flow chart illustrating a process performed according to an embodiment of the present system.

A process for capturing images according to an embodiment of the present system will now be described. A flow chart corresponding to a process performed by an embodiment of the present system is shown in FIG. 1B. The process 130 may be controlled by one more computers communicating directly and/or over a network. The process 130, as well as other process according to the present methods, may be performed by execution of instructions embodied on a computer readable medium (such as the memory 104) by a processor, such as the controller 102. The processor or controller 102 may be an application-specific or general-use integrated circuit(s). Further, the processor 102 may be a dedicated processor for performing in accordance with the present system or may be a general-purpose processor wherein only one of many functions operates for performing in accordance with the present system. The processor 102 may operate utilizing a program portion, multiple program segments, or may be a hardware device utilizing a dedicated or multi-purpose integrated circuit.

The process 130 may include one or more of the following steps, acts or operations. Further, one or more of these steps, acts, or operations may be combined and/or separated into sub-steps, sub-acts, or sub-operations, if desired. For the sake of clarity, the acts of the process 130 will hereinafter be referred to as "steps."

In step 132, a process for acquiring imaging information is activated and an image sequence is loaded. This image sequence may include image labels which may be unique (i.e., different from each other) and may correspond with a sequence shown in table 1 below, which is specific to a thyroid gland. However, other sequences are also envisioned. Moreover, sequences which may be unique to other organs are also envisioned. After completing step 132, the process continues to step 133.

TABLE 1

IMAGE

Right Lobe Transverse-superior (upper pole)
Right Lobe Transverse-mid pole
Right Lobe Transverse-inferior (lower pole)
Right Lobe Sagittal-lateral
Right Lobe Sagittal-mid
Right Lobe Sagittal-medial In step 133, the process may initialize various variables and/or counters. For example, the process may initialize the current image so that it corresponds with the first entry in sequence shown in table 1. Accordingly, in the present example, the current image may be set so that it corresponds with the first image in the sequence that was loaded in step 132 (i.e., the Right Lobe Transverse—superior (upper pole)). After completing step 133, the process continues to step 134. However, it is also envisioned that the process may start at other entries, if desired.

In step 134, the process may determine whether the current image has already been acquired. This step may be used so that a user may not need to acquire an image twice when a caliper is requested and a corresponding image is already available. If it is determined that the current image has been acquired, the process continues to step 138. If it is determined that the current image has not been acquired, the process continues to step 136.

In step 136, the process may output (e.g., via the display 106) a request to a user to input the current image. This request may include a blank image with a label of the current image. For example, if the current image is the first image in the sequence shown in table 1, the label would read "Right Lobe Transverse—superior (upper pole)". Accordingly, the display may display a request to input an "Input a Right Lobe Transverse—superior (upper pole) image." The system may also include the ability to output this request via, for example, the speaker. After completing step 136, the process continues to step 137. Of course, the label (or a list of labels) may be presented to the user for acceptance by the user, or for selection of a label by the user from among a list of labels.

In step 137, the process receives an image which corresponds with the current image. The process may wait to receive the image for a certain period of time or may wait an unlimited period of time, as desired, such as until user input is provided. When it is determined that the image has been received, the process associates the image with the corresponding label such as, for example, "Right Lobe Transverse—superior (upper pole)." After completing step 137, the process continues to step 138.

In step 138, the process determines whether the user has requested a caliper. To reduce the number of inputs, the process may determine that the user has requested a caliper when, for example, the user enters a predetermined caliper key. This predetermined key (either a hard of soft key) may correspond with a caliper mode request, or may correspond with a location input which may correspond with a location in the image. Thus, if the user selects a location input, the user may not need to request a caliper mode and thereafter select a location which may require two or more steps. If it is determined that the user has requested a caliper, the process continues to step 152. However, if it is determined that the user has not requested a caliper, the process continues to step 140.

In step 140, the process determines whether all images in the image sequence have been acquired. If it is determined that all images in the image sequence have been acquired, the process continues to step 144. However, it is determined that all images in the image sequence have not been acquired, the process continues to step 142.

In step 142, the process may advance to the next image in the sequence. Accordingly, the process may set the current image=the next image. However, it is also envisioned that the process may follow any other order. For example, the process may set the current image=previous image in the sequence, etc. After completing step 142, the process may repeat step 134.

In step 144, the process may process image information which may include the images which were acquired. The process may associate labels with each of the images, may associate the images with each other, etc. For example, the process may determine whether image information corresponding to a particular image contains coordinate information and may associate a related orthogonal image if the image information corresponding with a particular image contains image information. The process may then form a report which may include one or more of image information, label information, coordinate information, the processed information, etc. The process may then continue to step 146. The process may also compare the present report or parts thereof with corresponding parts of one or more previous reports or parts thereof.

In step 146, the process may display the current report and/or previous reports. The process may then continue to step 148.

In step 148, the process may save the current report and/or parts thereof.

In step 152, the process may associate caliper inputs and/or measurements with the current image. To enter a caliper input, the user may select a location in the current image with a pointing device and depress a predetermined key. The process may associate two caliper consecutive caliper inputs with each other so that a distance which corresponds with a distance that is between the locations of the two caliper inputs in the current image can be determined. For example, the process may associate first and second caliper inputs and determine a distance between these caliper inputs with respect to the current image. Then, the next two caliper inputs may then be associated with each other so as to determine a distance between these two inputs with respect to the current image. The process may wait a certain time during which a user may input distances. However, it is also envisioned that only a certain number of inputs may be entered, etc. The process may illustrate the selected locations in a corresponding image and include a legend which indicates distance between selected locations in the image. The selected coordinates/locations in an image may be identified using one or more identifiers such as, for example, "+," "x," etc. After completing step 152, the process continues to step 154.

In step 154, the process determines an image associated with anatomy. This associated image may be different for each iteration of the current process. This associated image can, for example, include an image which may have a distinguishing feature which may be different from a corresponding feature of the current image. For example, the associated image may represent an image having a plane which is orthogonal or substantially orthogonal to an image plane of the current image. For example if the current image corresponds with the Right Lobe Transverse—superior (upper pole) image, the associated image may correspond with a Right Lobe Sagittal—lateral image. After completing step 154, the process continues to step 156.

In step 156, the process may update the image sequence by placing the current associated image between the current image and the next image in the sequence. Thus, the process may modify the image sequence such that the Right Lobe Sagittal—lateral image immediately precedes the Right Lobe Transverse—mid pole in the image sequence shown in, for example, table 1. In the present embodiment, the associated image is an image which is orthogonal to the current image. The process may then set the current image=the associated image. After completing step 156, the process continues to step 158. It is also envisioned that the process may also swap positions of the associated image with the next image in which case, the Right Lobe Sagittal—lateral image and the Right Lobe Transverse—mid pole images in the sequence shown in Table 1 may be swapped. When swapping, image information which corresponds with each entry may also be swapped so that images and corresponding information such as labels, etc. are also swapped.

In step 158, the process may output a request to a user to input the current image. The process may then receive an image which corresponds with the current image. The process may wait to receive the image for a certain period of time or may wait an unlimited period of time, as desired. When it is determined that the image has been received, the process may associate the image with the corresponding label such as, for example, "Right Lobe Sagittal—lateral." After completing step 158, the process continues to step 160. It is also envisioned that the process may determine whether an image which corresponds with the current image has already been acquired, and, if so, display the image rather than request that the user input the image.

In step 160, the process may display a caliper and/or may request that the user enter a caliper input. After completing step 160, the process continues to step 162.

In step 162, the process may associate one or more caliper inputs with the current image. To enter a caliper input, the user may select a location in the current image with a pointing device and depress a predetermined key. This step may be similar to step 152. After completing step 162, the process repeats step 140.

Thus, according to the present system, when a user enters a caliper input corresponding to a selected image, the system may request that the user input an associated orthogonal image and/or a caliper input corresponding to the associated orthogonal image. Accordingly, immediately after a user enters a measurement/location of one or more abnormalities (or location of interest) with regard to a specific image, an orthogonal image is presented to the user for measurement/location of the same abnormalities (or location of interest) in a different plane. Thus, the location and/or size of abnormalities and/or other locations of interest can be easily and conveniently recorded. The system may then form a report including this information.

Figure 2:
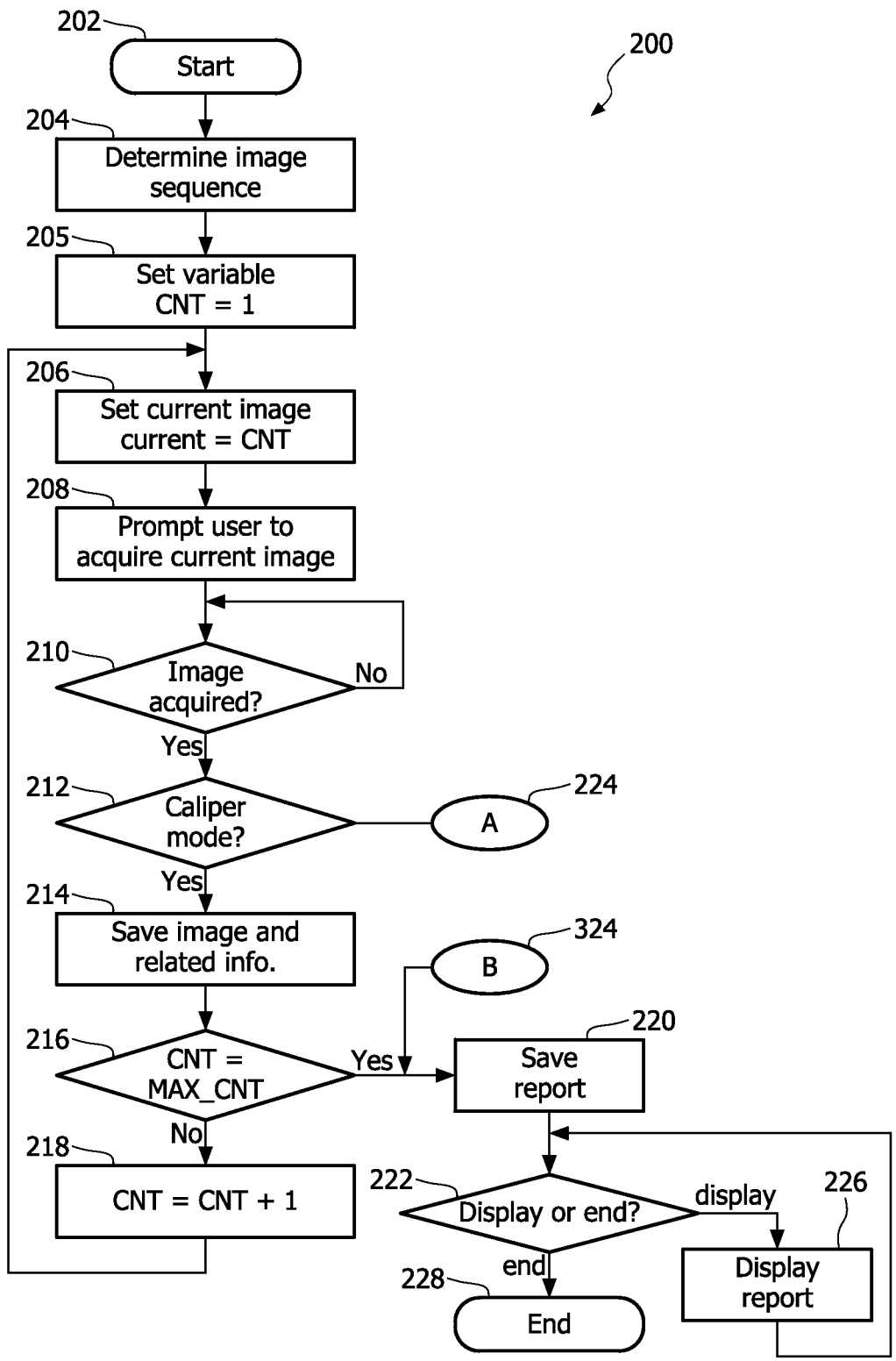
FIG. 2 is a flow chart illustrating a process performed according to another embodiment of the present system.

A process for capturing images according to the present system will now be described. A flow chart corresponding to a process 200 performed by an embodiment of the present system is shown in FIG. 2. The process 200 may be controlled by one more computers communicating directly and/or over a network. The process 200 may include one or more of the following steps, acts or operations. Further, one or more of these steps, acts, or operations may be combined and/or separated into sub-steps, sub-acts, or sub-operations, if desired. For the sake of clarity, the acts of process 200 will hereinafter be referred to as "steps."

In step 202, a process for acquiring imaging information is activated. After completing step 202, the process continues to step 204.

In step 204, the controller determines an image sequence. This image sequence may then be used to prompt a user to acquire images according to a predetermined order as will be described below. The image sequence may be determined using a look-up table, via a user's input, or by using any other suitable method. For example, a look-up table may include an image sequence such as shown in Tables 2A and 2B below. However, it is also envisioned that other image sequences may be defined and/or used. For example, Table 2B illustrates an alternative image sequence different from the sequence shown in Table 2A. Further, it is envisioned that a user may be prompted to input a desired image sequence (e.g., 1, 3, 4, 6, 5, 2). This image sequence may then be stored in a look-up table for later use. Accordingly, the process may refer to one or more desired look-up tables, each corresponding to a desired image sequence. Further, the process may determine which of the one or more look-up tables to refer to either automatically, or based on, for example, a user's input. The look-up tables may be specific to an organ. For example, each organ may include its own unique table. Thus, the controller may determine a table to be used based upon, for example, a user's selection of an organ. However, this selection may also be preset.

TABLE 2A

| SEQUENCE | IMAGE |
|---|---|
| 1 | Right Lobe Transverse-superior (upper pole) |
| 2 | Right Lobe Transverse-mid pole |
| 3 | Right Lobe Transverse-inferior (lower pole) |
| 4 | Right Lobe Sagittal-lateral |
| 5 | Right Lobe Sagittal-mid |
| 6 | Right Lobe Sagittal-medial |

TABLE 2B

| 1 | Right Lobe Transverse-superior (upper pole) |
|---|---|
| 2 | Right Lobe Transverse-mid pole |
| 3 | Right Lobe Transverse-inferior (lower pole) |
| 4 | Right Lobe Sagittal-lateral |
| 5 | Right Lobe Sagittal-mid |
| 6 | Right Lobe Sagittal-medial |
| 7 | Left Lobe Transverse-superior (upper pole) |
| 8 | Left Lobe Transverse-mid pole |
| 9 | Left Lobe Transverse-inferior (lower pole) |
| 10 | Left Lobe Sagittal-lateral |
| 11 | Left Lobe Sagittal-mid |
| 12 | Left Lobe Sagittal-medial |
| 13 | Isthmus-transverse |
| 14 | Isthmus-sagittal |

With reference to Table 2A, the image sequence in the following process may begin with the first input, i.e., a Right Lobe Transverse—superior upper pole image. Table 2A may also include variables such as a MAX_CNT variable which may indicate a total number of images in the image sequence or a desired maximum number of images which may be set by, for example, the user. With reference to Table 2A, MAX_CNT may be set such that it is equal to the number of images in the image sequence of Table 2A. However, other methods for determining a maximum number of images are also envisioned. For example, a user may set MAX_CNT=3, in which case the image sequence may end after an image corresponding with the Right Lobe Transverse—inferior (lower pole) view has been acquired, or the controller may determine MAX_CNT based upon an evaluation of, for example, Table 2A. After completing step 204, the process continues to step 205. With reference to Table 2B, MAX_CNT may be set to 14, if desired.

In step 205, variables may be set. In the present example, an optional image count variable (CNT) is set to an initial value.

For example, CNT may be set=1. The process may also determine, set and/or request the user to and/or set the MAX_CNT variable in this step. After completing step 205, the process continues to step 206.

In step 206, the process may set the current image. For example, the controller may set a current image variable CURRENT, which corresponds with a current image, so that it is equal to CNT. Thus, with reference to Table 2A, by setting CURRENT=CNT (which is =1 for the first iteration), then the current image would correspond with the Right Lobe Transverse superior (upper pole) as shown in Table 2A. After completing step 206, the process may continue to step 208.

In step 208, the process may prompt a user to acquire the current image. Accordingly, the controller 102 may output, via the display 106 or SPK 112, information which may identify a desired image. Thus, with reference to Table 2A and assuming CNT=1, and that CURRENT=CNT=1, the user may be prompted to acquire the Right Lobe Transverse superior (upper pole) when CNT=1. Accordingly, the display may highlight or otherwise display information to inform a user of the desired current image and may request that a user perform acts necessary to acquire this image using, for example, the image acquisition probe (e.g., see, 114). Thus, the display may display information corresponding with an image sequence such as, for example, is shown in Table 2A and highlight the desired current image. The process may wait to receive corresponding image information from the image acquisition probe. After completing step 208, the process continues to step 210.

In step 210, the process determines whether the desired image information has been acquired (i.e., input). Accordingly, if the process determines that the desired image information (or sufficient parts thereof) has been acquired, the process continues to step 212. However, if the process determines that the desired image information (or sufficient parts thereof) has not been acquired, step 210 may be repeated.

In step 212, the process determines whether a caliper mode has been requested. The caliper mode may be requested by the controller or by a user's input, such as when a region of interest (e.g., an abnormality) is automatically detected by the controller by comparing the current image with an expected image(s) stored in the memory 104 and/or memory 122 shown in FIG. 1A. Further, an icon or other image may be output (e.g., via the display 106 or SPK 112) for a user's selection. If it is determined that the caliper mode has been requested, then the process continues to step 224 (see A). However, if the process determines that the caliper mode has not been requested, then the process may continue to step 214.

In step 214, the process saves the currently acquired image and related information. For example, the image may be saved with information such as, for example, labels, annotations, day, date, time, and caliper information such as, for example, locations coordinates, measurements. After step 214 is completed, the process may continue to step 216.

In step 216, the process determines whether the current image information corresponds with a last image (e.g., selection 6—the Right Lobe Sagittal—medial selection in Table 2A). Thus, the process may determine whether CNT=MAX_CNT. If it is determined that CNT=MAX_CNT, the process may continue to step 220. However, if the process determines that CNT is not equal to MAX_CNT, then the process may continue to step 218. It is also envisioned that other tables, orders, and/or variables may be used (e.g., first-to-last, last-to-first, etc.), etc. Moreover, the user may also enter an input to indicate that the current image is a last image. Thus, the process may branch based upon an input of a user.

In step 218, the process may set the current image to correspond with the next image. The process may do this by incrementing an image counter such as, for example, current image=current image+1. Accordingly, the process may increment CNT such that CNT=CNT+1. However, the process may also use other routines to determine a current image and a next image. After completing step 218, the process may repeat step 206.

In step 220, the process may process acquired images and related information and saves a corresponding report. The related information may include corresponding labels and/or caliper information such as, caliper information including coordinate information. The process may then continue to step 222.

In step 222, the process may determine whether it should display the corresponding report or end. If it is determined that the process should end, the process may continue to step 228, where it ends. However, if the process determines that it should display the corresponding report, the process may continue to step 226.

In step 226, the process may retrieve information related to the corresponding report and display this information as shown and described below with respect to FIG. 4. The process may then return to step 222. The process may also receive from the user a request to display another report, in which case, the process may display the requested report. Further, the process may compare previous reports with the current report.

Figure 3:
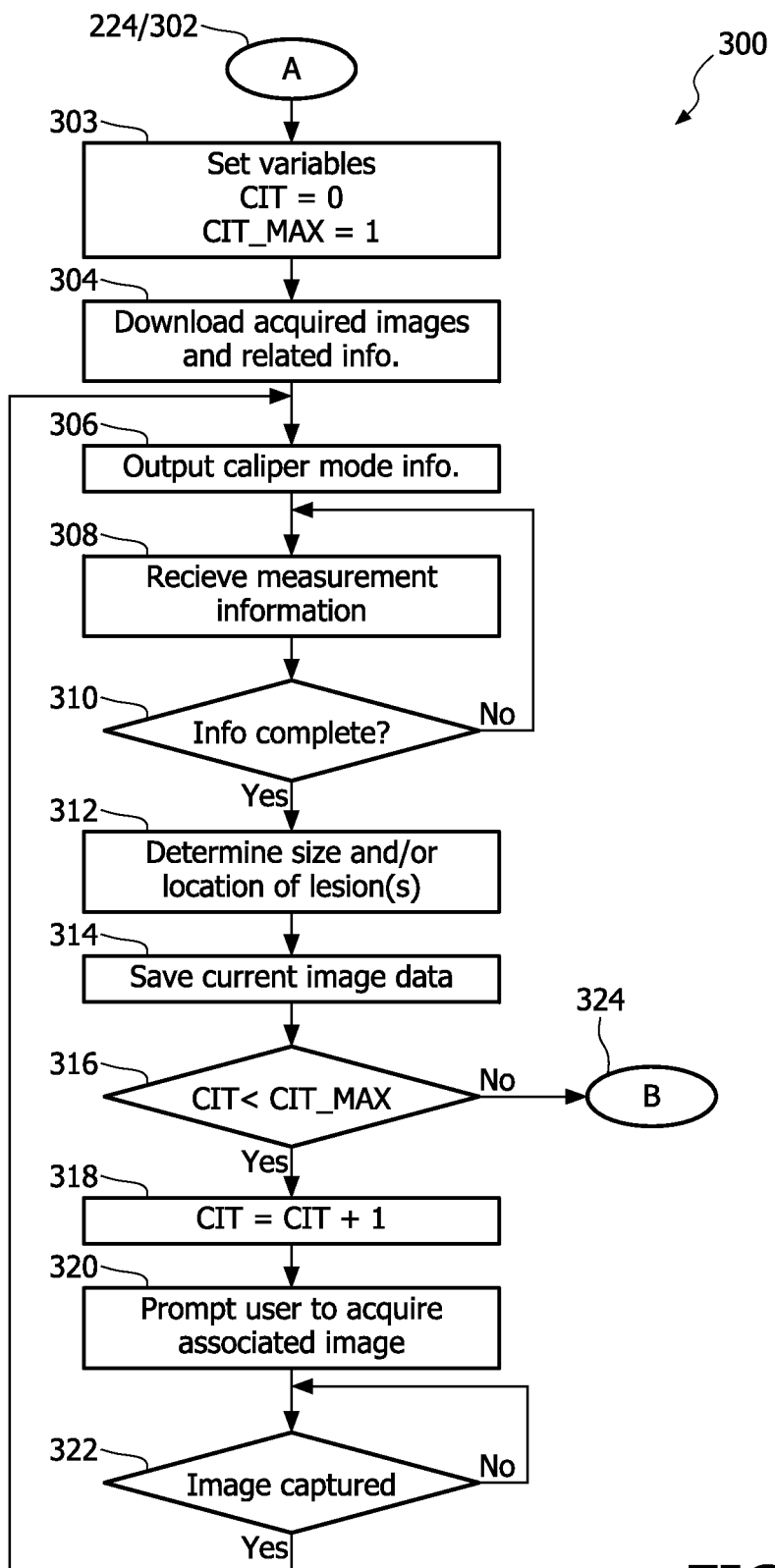
FIG. 3 is a flow chart illustrating a process performed according to yet another embodiment of the present system.

A flow chart illustrating a process performed according to an embodiment of the present system is shown in FIG. 3. A process 300 which may be performed when a caliper mode is called according to the present system will now be described. The process 300 may be controlled by one more computers communicating directly and/or over an optional network. The process 300 may include one or more of the following steps, acts or operations. Further, one or more of these steps, acts, or operations may be combined and/or separated into sub-steps, -acts, or -operations, if desired.

In step 224/302 which is branched off step 212 in FIG. 2, the process 300 enters a caliper mode and continues to step 303.

In step 303, the process may set one or more iteration variables which may be used to determine a number of times certain steps may be repeated. For example, in the present example, a caliper iteration variable (CIT) may be set=0 and the maximum number of iterations (CIT_MAX) may be set=1 or any desired number. Further, one or more of these variables may be set by, for example, a manufacturer, a user, etc. to other predetermined variables, as desired. Further, the controller may determine settings for these variables based upon user settings, previous usage history, etc. It is also envisioned that other variables and/or settings may be used. After completing step 303, the process may continue to step 304.

In step 304, the process may download acquired images, and related information may be used in the caliper mode. For example, in the caliper mode the process may magnify the display of the current image. The related information may include information related to a current image (e.g., the image, annotations, measurements, scaling. After completing step 304, the process may continue to step 306.

In step 306, the process may output caliper mode information using any suitable method such as, for example, a visual method (e.g., via a display) and/or an audible method (e.g., via SPK). For example, in the current embodiment, the process may output caliper mode information by displaying a caliper input and the current image (i.e., an image corresponding with the current CNT) which may have been received from the image acquisition probe. The caliper mode information may include a message indicating that "Add Measurements" has been activated. After completing step 306, the process may continue to step 308.

In step 308, the process receives measurement information corresponding to a desired object or location in the current image. For example, the measurement information may correspond with locations and/or size of one or more abnormalities (e.g., each of which may correspond with a thyroid lesion, etc.) which are displayed in the present image. The measurement information may be processed by, for example, using any suitable analysis software such as, for example, QLAB™, which may determine certain imaging parameters such as depth, focal zone location compression, contours, x, y, and/or z coordinates, velocity information (from Doppler techniques), and/or echo intensity. After receiving and/or processing the measurement information, the process may continue to step 310.

In step 310, the process determines whether measurement information (i.e., coordinate information) and/or other information which may be desired (e.g., annotations, etc.) has been input. If the process determines that measurement information has been input, the process continues to step 312. However, if the process determines that complete measurement information has not been input, the process may repeat step 308.

In step 312, the process may determine the size and/or location of one or more areas corresponding with the measurement information. These areas may correspond with lesions, e.g., physical abnormalities, or may correspond with a selected area that a medical professional wishes to analyze further. The measurement information may be further processed by, for example, using any suitable analysis software such as, for example, QLAB™, which may determine certain imaging parameters such as depth, focal zone location compression, contours, x, y, and/or z coordinates, velocity information (from Doppler techniques), and/or echo intensity. After completing step 312, the process continues to step 314.

In step 314, the process 300 processes the image and related information and may save this information in a corresponding report. Thus, the process may automatically associate annotations and measurements with corresponding image data (i.e., the current image). Accordingly, annotations and measurements will be associated with the corresponding image data. The process may then continue to step 316.

In step 316, the process determines whether it should acquire another image relating to the current image. Accordingly, the process may determine whether CIT is less than CIT_MAX. If it is determined that CIT is less than CIT_MAX, the process may continue to step 318. However, if it is determined that CIT is equal to (or greater than) CIT_MAX, the process may continue to step 324.

In step 318, the process may increment CIT. For example, the process may increment CIT such that CIT=CIT+1. The process may then continue to step 320.

In step 320, the process may prompt a user to acquire another image (i.e., a next image) which may be associated with the previously captured image. This other image may then be set as a current image. The process may visually and/or audibly output information informing a user of a desired image by displaying or otherwise outputting, for example, a message such as, "Please Acquire a Right Lobe Sagittal—Mid image." The user may then obtain an image which corresponds with the output message.

According to the present embodiment, the process may determine that the next image (i.e., CIT+1) may be, for example, orthogonal to the previous image. Thus, if the process determines that the previous image (i.e., CIT before incrementing) was a Right Lobe Transverse—Superior (Upper Pole) image, the process may determine that the next image (i.e., CIT+1) may be set to a Right Lobe Sagittal—lateral image. The process may determine a current image by using a look-up table or other suitable method. For example, the process may use a look-up table as shown in Table 3 below. Of course, the process any use or follow other sequences, where the next image is defined according to a desired protocol, such as instructions embodied in a computer readable medium for execution by the processor 102 for performing operations for data acquisition and control according to the one embodiment of the present methods, systems and devices. The examination or process is over when the last image defined by the protocol is acquired and processed, such as when the value for MAX_CNT is reached, as described in connection with Tables 2A, 2B.

TABLE 3

| SEQ. | CURRENT IMAGE (CIT) | NEXT IMAGE (CIT +1) |
|---|---|---|
| 1 | Right Lobe Transverse-superior (upper pole) | Right Lobe Sagittal-lateral |
| 2 | Right Lobe Transverse-mid pole | Right Lobe Sagittal-mid |
| 3 | Right Lobe Transverse-inferior (lower pole) | Right Lobe Sagittal-medial |
| 4 | Right Lobe Sagittal-lateral | Right Lobe Transverse-superior (upper pole) |
| 5 | Right Lobe Sagittal-mid | Right Lobe Transverse-mid pole |
| 6 | Right Lobe Sagittal-medial | Right Lobe Transverse -inferior (lower pole) |

Table 3 may include next images which may be set by the manufacturer, a user, by the controller based upon stored previous usage history, etc. Table 3 may also be incorporated into Table 2A or vice versa. Further, each selection may include information indicating its orthogonality with respect to another image or displayed view. For example, each cell may include a flag indicating orthogonality. The process may also keep track of images which have already been captured. Thus, for example, if an image has been captured, the system may display this acquired image rather than request that a user acquire the image. While displaying the image, a user may input caliper data/information.

After completing step 320, the process may continue to step 322.

In step 322, the process may determine whether the current image has been captured. If the process determines that the current image has been captured, the process may repeat step 306. However, if the process determines that the current image has not been captured, the process may repeat step 322.

Figure 4:
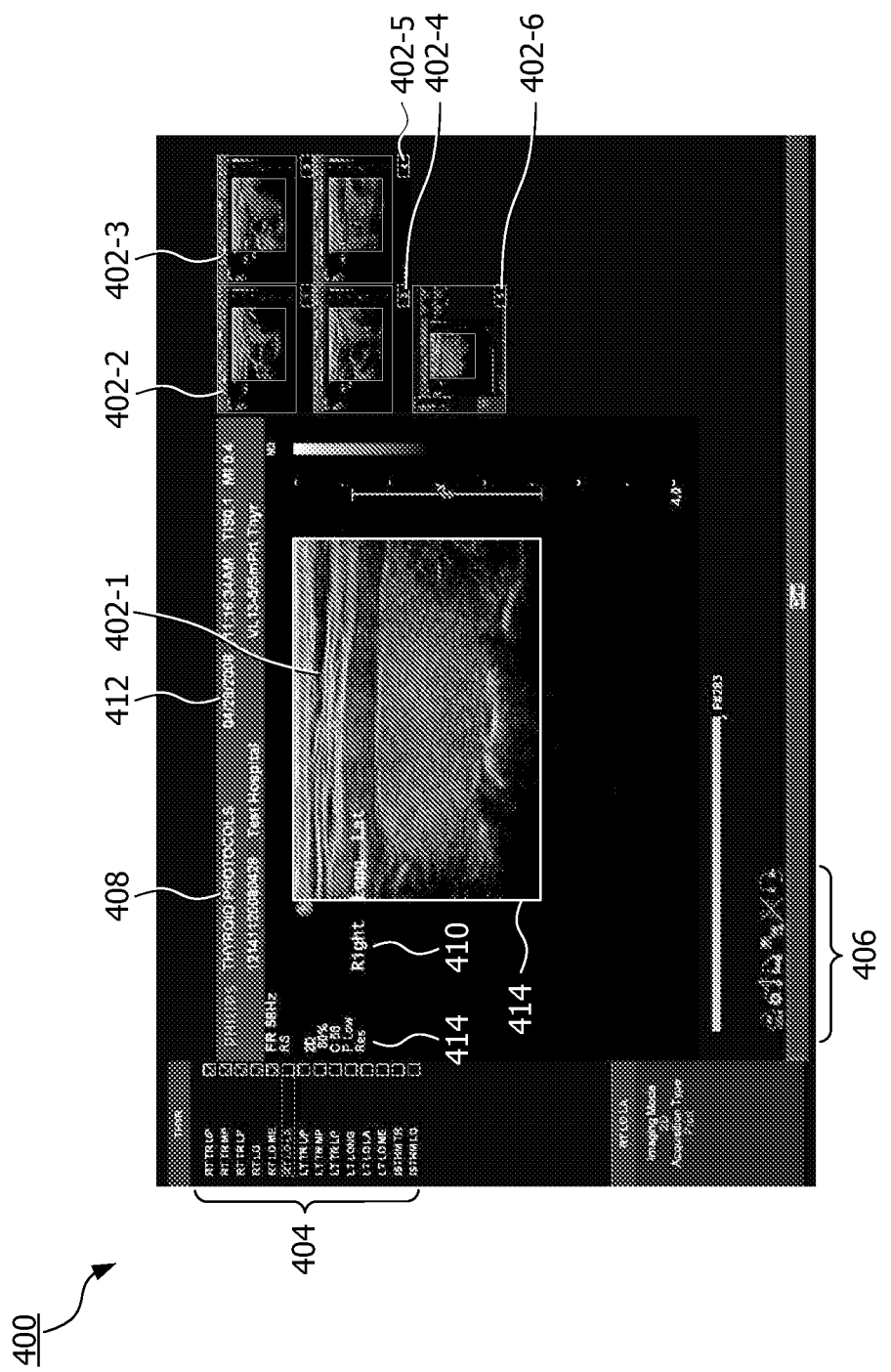
FIG. 4 is a screen shot illustrating an image-capture process according to the present system.

A screen shot 400 illustrating an image capture process according to the present system is shown in FIG. 4. The screen shot 400 illustrates a screen which may be displayed using data which may have been saved in a report. This data may include acquired image data, notes, annotations, measurements, day, date, time, patient's identification (ID), such as, for example, a number, a name, etc., medical professional data (e.g., sonographer's name, doctor's name, medical center's name, location, etc.), viewing/editing history, etc. The screen 400 may include images 402-1 to 402-6, associated view selections 404, and user selections 406. Each of the images 402-x (where x=1-6 in FIG. 5) may include information such as, for example, hospital information 408, view type (e.g., Right Longitudinal Lateral) 410, time/date information 412, primary image information 414, and/or other information, as needed. A small image (or likeness) of each of the other images 402-x may be displayed in a smaller format for a user's convenience. Selecting one of the other images may cause the display of this other image in lieu of the previously selected main image, which may be displayed as a small image. Further, a compare setting may be used, in which case, for example, complementary orthogonal views or other selected views may be displayed in a window that is larger than windows which display the other images in small views.

The user selections 406 may include individual icons or menu items which may be selected by the user to, for example, scan, file, print, transfer images (e.g., from one display to another), mute, transcribe, and/or use a headpiece, as desired. The displayed images and associated data may be saved at any time during the process shown in FIGS. 3 and/or 4 or may be updated later. However, a history may be activated to indicate when data may have been added and/or edited so that a user may refer back to original information.

Figure 5:
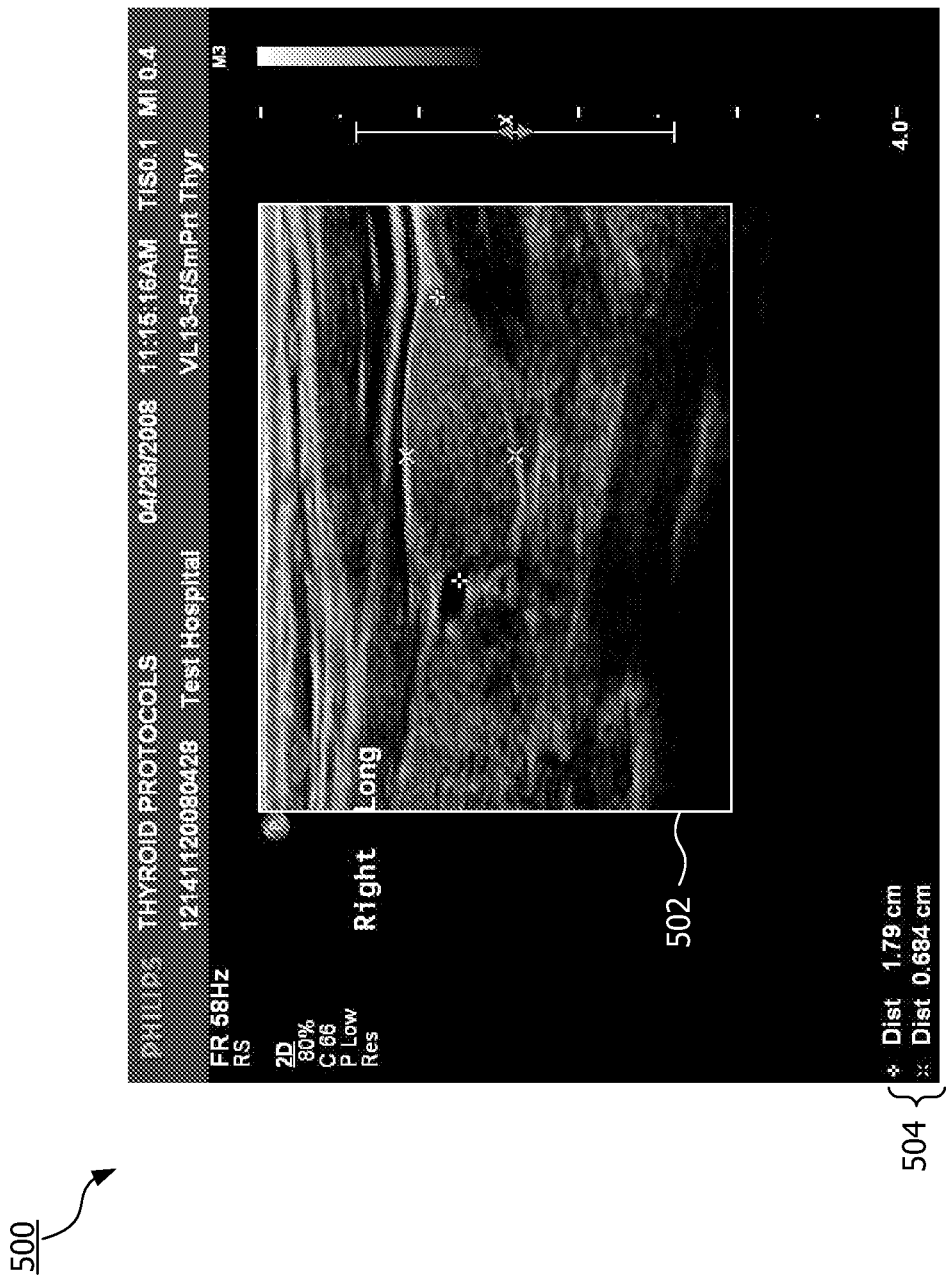
FIG. 5 is a screen shot illustrating a caliper measurement process according to the present system.

A screen shot 500 illustrating a caliper measurement process according to the present system is shown in FIG. 5. The screen shot 500 may include an image which corresponds with one of the images 402-x shown in FIG. 4. However, in FIG. 5, a caliper mode has been activated so that a user can input necessary location information which may correspond with points of interest such as, for example, "X" and "+" shown in an image 502. The location information may include, for example, displacement measurements 504, such as the distances between the points of interest, which may be saved with the corresponding images, corresponding information such as caliper information, and other information may be saved for later use.

Thus, according to the present systems and devices, an accurate, convenient, low-cost, upgradeable, reliable, and standardized imaging system is provided.

Although the present system has been described with reference to a thyroid ultrasound imaging system, it is also envisioned that the present system can be extended to other medical imaging systems where multiple images are obtained in a systematic manner. Accordingly, the present system may be used to obtain and/or record image information related to renal, testicular, breast, ovarian, uterine, thyroid, hepatic, splenic, heart, arterial and vascular system, as well as other imaging applications. Further, the present system may also include a program which may be used with conventional imaging systems so that they may provide features and advantages of the present system.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and devices is that conventional medical image systems can be easily upgraded to incorporate the features and advantages of the present systems and devices.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of elements or acts other than those listed in a given claim;

b) the word "a" or "an" preceding an element does not exclude the presence of a plurality of such elements;

c) any reference signs in the claims do not limit their scope;

d) several "means" may be represented by the same item or by the same hardware- or software-implemented structure or function;

e) any of the disclosed elements may be comprised of hardware portions (e.g., including discrete and integrated electronic circuitry), software portions (e.g., computer programs), and any combination thereof;

f) hardware portions may be comprised of one or both of analog and digital portions;

g) any of the disclosed devices or portions thereof may be combined or separated into further portions unless specifically stated otherwise;

h) no specific sequence of acts or steps is intended to be required unless specifically indicated; and i) the term "plurality of" an element includes two or more of the claimed element, and does not imply any particular range or number of elements; that is, a plurality of elements may be as few as two elements, and may include an immeasurable number of elements.

What is claimed is:

1. An imaging system, comprising:
an ultrasonic probe; and
a controller which:
(a) receives information related to a first sequence of a plurality of images to be acquired in a predetermined order according to an exam protocol specific to an organ or vessels being assessed;
(b) receives, from the ultrasonic probe, iteratively, for each image of the plurality of images to be acquired in the first sequence, image information corresponding to a current image of the plurality of images in the first sequence;
(c) determines, for each iteration with the current image, whether a caliper input has been received, and when it is determined that a caliper input has been received:
(c)(i) obtains coordinate information corresponding to one or more locations of interest in the current image,
(c)(ii) selects a further image to be acquired which is different from, and associated with, the current image, acquires the further image, and includes the further image in a second sequence of images, wherein the second sequence of images comprises the first sequence of images modified to include the further image placed between the current image and a next image to be acquired in the first sequence, and
(c)(iii) obtains coordinate information corresponding to the one or more locations of interest in the further image of the second sequence of images; and
(d) saves a report that comprises (d)(i) the image information and (d)(2) the coordinate information corresponding to the one or more locations of interest, for (d)(iii) each image of the plurality of images of the first sequence and (d)(iv) each further image of the second sequence of images.

2. The imaging system of claim 1, wherein the further image corresponds with an image plane which is substantially orthogonal to an image plane of the current image.

3. The imaging system of claim 1, wherein the controller associates a unique view label with each image of the plurality of images.

4. The imaging system of claim 1, wherein the controller receives, from the ultrasonic probe, the further image.

5. The imaging system of claim 1, wherein the controller outputs a request that coordinate information corresponding to one or more locations in the further image be input.

6. A data acquisition method performed by a controller, the method comprising the acts of:
   (a) receiving information related to a first sequence of a plurality of images be acquired in a predetermined order according to an exam protocol specific to an organ or vessels being assessed;
   (b) receiving, from an ultrasonic probe, iteratively, for each image of the plurality of images to be acquired in the first sequence, image information corresponding to a current image of the plurality of images in the sequence;
   (c) determining, for each iteration with the current image, whether a caliper input has been received, and when it is determined that a caliper input has been received:
      (c)(i) obtaining coordinate information corresponding to one or more locations of interest in the current image,
      (c)(ii) selecting, by the controller, a further image to be acquired which is different from, and associated with, the current image, acquiring the further image and including the further image in a second sequence of images, wherein the second sequence of images comprises the first sequence of images modified to include the further image placed between the current image and a next image to be acquired in the first sequence, and
      (c)(iii) obtaining coordinate information corresponding to one or more locations of interest in the further image of the second sequence of images; and
   (d) saving a report that comprises (d)(i) the image information and (d)(ii) the coordinate information corresponding to the one or more locations of interest, for (d)(iii) each image of the plurality of images of the first sequence and (d)(iv) each further image of the second sequence of images.

7. The data acquisition method of claim 6, wherein the further image corresponds with an image plane which is substantially orthogonal to an image plane of the current image.

8. The data acquisition method of claim 6, further comprising the act of associating a unique view label with each image of the plurality of images.

9. The data acquisition method of claim 8, further comprising the acts of displaying a caliper or outputting a request that one or more coordinates corresponding to one or more locations in the further image be input, when the further image is received.

10. A non-transitory computer-readable-medium embodied with a computer program executable by a controller for receiving image information from an ultrasonic probe, the computer program comprising:
   a program portion configured to (a) receive information related to a sequence of a plurality of images to be acquired in a predetermined order according to an exam protocol specific to an organ or vessels being assessed;
   a program portion configured to (b) receive, from an ultrasonic probe, iteratively, for each image of the plurality of images to be acquired in the first sequence, image information corresponding to a current image of the plurality of images in an image sequence;
   a program portion configured to (c) determine, for each iteration with the current image, whether a caliper input has been received, and when it is determined that a caliper input has been received:
      (c)(i) to obtain coordinate information corresponding to one or more locations of interest in the current image,
      (c)(ii) to select, by the controller, a further image which is different from, and associated with, the current image, acquire the further image and include the further image in a second sequence of images, wherein the second sequence of images comprises the first sequence of images modified to include the further image placed between the current image and a next image to be acquired in the first sequence, and
      (c)(iii) to obtain coordinate information corresponding to one or more locations of interest in the further image of the second sequence of images; and
   a program portion configured to (d) save a report that comprises (d)(i) the image information and (d)(ii) the coordinate information corresponding to the one or more locations of interest, for (d)(iii) each image of the plurality of images of the first sequence and (d)(iv) each further image of the second sequence of images.

11. The non-transitory computer-readable-medium embodied with a computer program of claim 10, wherein the further image corresponds with an image plane which is substantially orthogonal to an image plane of the current image.

12. The non-transitory computer-readable-medium embodied with a computer program of claim 10, further comprising a program portion configured to associate a unique view label with each image of the plurality of images.

13. The non-transitory computer-readable-medium embodied with a computer program of claim 10, further comprising a program portion configured to output a request that one or more coordinates corresponding to one or more locations in the further image be input.

* * * * *